(12) United States Patent
Hommeltoft (10) Patent No.: US 10,435,337 B2
(45) Date of Patent: Oct. 8, 2019

(54) COMPOSITION OF ISOALKANE ALKYLATE BASE OIL

(71) Applicant: Chevron U.S.A. Inc., San Ramon, CA (US)

(72) Inventor: Sven Ivar Hommeltoft, Pleasant Hill, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 112 days.

(21) Appl. No.: 15/837,324

(22) Filed: Dec. 11, 2017

(65) Prior Publication Data

US 2018/0105762 A1    Apr. 19, 2018

Related U.S. Application Data

(60) Division of application No. 15/159,205, filed on May 19, 2016, now Pat. No. 10,093,594, and a continuation of application No. 15/158,916, filed on May 19, 2016, now abandoned, and a continuation of application No. 15/158,750, filed on May 19, 2016, now abandoned, and a continuation of application No. 15/730,872, filed on Oct. 12, 2017, now Pat. No. 10,246,384, which is a division of application No. 15/159,161, filed on May 19, 2016, now Pat. No. 9,822,046.

(51) Int. Cl.
*C10M 105/04* (2006.01)
*C07C 2/62* (2006.01)

(52) U.S. Cl.
CPC .............. *C07C 2/62* (2013.01); *C10M 105/04* (2013.01); *C07C 2531/02* (2013.01); *C10M 2203/022* (2013.01); *C10N 2220/022* (2013.01); *C10N 2220/028* (2013.01); *C10N 2270/00* (2013.01)

(58) Field of Classification Search
CPC combination set(s) only.
See application file for complete search history.

(56) References Cited

U.S. PATENT DOCUMENTS

| | | | |
|---|---|---|---|
| 6,066,603 A * | 5/2000 | Emert | C08F 10/00 44/393 |
| 6,233,157 B1 | 11/2001 | Carpenter et al. | |
| 7,285,698 B2 | 10/2007 | Liu et al. | |
| 7,432,408 B2 | 10/2008 | Timken et al. | |
| 7,432,409 B2 | 10/2008 | Elomari et al. | |
| 7,495,144 B2 | 2/2009 | Elomari | |
| 7,520,976 B2 | 4/2009 | Miller et al. | |
| 7,531,707 B2 | 5/2009 | Harris et al. | |
| 7,572,944 B2 | 5/2009 | Elomari et al. | |
| 7,973,204 B2 | 7/2011 | Elomari et al. | |
| 8,124,821 B2 | 2/2012 | Elomari et al. | |
| 8,198,484 B2 | 6/2012 | Martinez et al. | |
| 8,222,471 B2 | 7/2012 | Elomari et al. | |
| 8,268,762 B2 | 9/2012 | Fujita | |
| 8,399,390 B2 | 3/2013 | Wu et al. | |
| 8,436,221 B2 | 5/2013 | Hommeltoft et al. | |
| 8,497,404 B1 | 7/2013 | Hommeltoft et al. | |
| 8,669,403 B2 | 3/2014 | Fisher et al. | |
| 9,115,327 B2 | 8/2015 | Miller et al. | |
| 9,193,653 B1 | 11/2015 | Hommeltoft | |
| 2007/0142684 A1 | 6/2007 | Elomari et al. | |
| 2007/0142685 A1 | 6/2007 | Elomari et al. | |
| 2007/0142690 A1 | 6/2007 | Elomari | |
| 2007/0142691 A1 | 6/2007 | Elomari et al. | |
| 2008/0103071 A1 | 5/2008 | Tsai et al. | |
| 2009/0181872 A1 | 7/2009 | Yamada | |
| 2009/0240012 A1 | 9/2009 | Patil et al. | |
| 2010/0025296 A1 | 2/2010 | Hommeltoft | |
| 2010/0210745 A1 * | 8/2010 | McDaniel | C09D 5/008 521/55 |
| 2011/0054209 A1 | 3/2011 | De Kraker | |
| 2011/0144399 A1 | 6/2011 | Elomari et al. | |
| 2011/0319695 A1 | 12/2011 | Hommeltoft et al. | |
| 2012/0160740 A1 | 6/2012 | Zhan et al. | |
| 2013/0066130 A1 | 3/2013 | Luo et al. | |
| 2014/0148624 A1 | 5/2014 | Ohler et al. | |
| 2014/0221258 A1 * | 8/2014 | Ohler | C07C 5/05 508/110 |

FOREIGN PATENT DOCUMENTS

| | | |
|---|---|---|
| CN | 101177643 A | 5/2008 |
| WO | 2010129147 | 11/2010 |
| WO | 2014168403 A1 | 10/2014 |
| WO | 2016064853 | 4/2016 |

* cited by examiner

*Primary Examiner* — Ellen M McAvoy
*Assistant Examiner* — Chantel L Graham
(74) *Attorney, Agent, or Firm* — Terrence M. Flaherty (57) ABSTRACT

An isoalkane alkylate base oil consisting predominantly of long carbon chain molecules having a straight chain of no less than 12 carbons and having at least one branch towards the middle of the straight chain, and characterized by:
  a) containing <10 wt % n-alkanes, <0.1 wt % olefinic hydrocarbons, and <0.1 wt % aromatic hydrocarbons;
  b) the at least one branch is a branched alkyl group containing 4 or more carbon atoms; and
  c) the long carbon chain molecules have two terminal linear unbranched alkyl groups each containing at least 4 carbons. Also, an isoalkane alkylate base oil, characterized by having a total integral of the $^{13}$C NMR spectrum wherein more than 25% of the total integral of the $^{13}$C NMR spectrum falls within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+ (29.6-29.8 ppm).

10 Claims, 1 Drawing Sheet

COMPOSITION OF ISOALKANE ALKYLATE BASE OIL

This application is a divisional of U.S. application Ser. No. 15/159,205 titled: "HIGH VISCOSITY INDEX LUBRICANTS BY ISOALKANE ALKYLATION", filed on May 19, 2016, in Art Unit 1772, herein incorporated in its entirety.

This application is a continuing application to three previously co-filed applications, filed on May 19, 2016, titled: "BASE OIL HAVING HIGH VISCOSITY INDEX FROM ALKYLATION OF DIMER KETONE-DERIVED OLEFIN" (Ser. No. 15/158,750), "FARNESANE ALKYLATION" (Ser. No. 15/159,161), and "ALKYLATION OF METALLOCENE-OLIGOMER WITH ISOALKANE TO MAKE HEAVY BASE OIL" (Ser. No. 15/158,916), all herein incorporated in their entireties.

This application is a continuing application to U.S. application Ser. No. 15/730,872, titled "ALKYLATE BASE OIL OF BIOLOGICAL ORIGIN", filed on Oct. 12, 2017, herein incorporated in its entirety.

TECHNICAL FIELD

This application is directed to compositions of an isoalkane alkylate base oil and a process for alkylating an isoalkane with a linear olefin to produce an essentially aromatics and olefin-free alkylate base oil. The isoalkane alkylate base oil produced can consist predominantly of a mixture of isoalkanes in the base oil boiling range. An isoalkane alkylate base oil with a viscosity index in the Group III+ range is attainable.

SUMMARY

This application provides a process to make an isoalkane alkylate base oil having a VI higher than 90, comprising:
  a. selecting an isoalkane feed containing at least one isoalkane and an olefin feed containing at least one linear olefin such that a combined carbon number of the isoalkane feed and the olefin feed ($N_{alkane+olefin}$) is from 20 to 60;
  b. alkylating the isoalkane feed with the olefin feed in the presence of an acidic alkylation catalyst under alkylation conditions to make the isoalkane alkylate base oil having the VI higher than 90, wherein the isoalkane alkylate base oil has a kinematic viscosity at 100° C. from 2 to 30 mm²/s, a pour point less than 0° C., and a bromine index less than 2000 mg Br/100 g.

This application also provides an isoalkane alkylate base oil that is essentially free of olefins and aromatics and consists predominantly of long carbon chain molecules having a straight chain of no less than 12 carbon atoms and having at least one branch towards the middle of the straight chain, and characterized by:
  a) the isoalkane alkylate base oil contains less than 10 wt % n-alkanes, less than 0.1 wt % olefinic hydrocarbons, and less than 0.1 wt % aromatic hydrocarbons;
  b) the at least one branch is a branched alkyl group containing 4 or more carbon atoms; and
  c) the long carbon chain molecules have two terminal linear unbranched alkyl groups each containing at least 4 carbons.

This application also provides an isoalkane alkylate base oil, characterized by having a total integral of the $^{13}$C NMR spectrum wherein more than 25% of the total integral of the $^{13}$C NMR spectrum falls within $^{13}$C resonances in ranges for linear long chain alkyl groups given by: C1(13.9-14.2 ppm), C2(22.6-22.8 ppm), C3(31.9-32.05 ppm), C4(29.35-29.45 ppm), and C5+(29.6-29.8 ppm).

The present invention may suitably comprise, consist of, or consist essentially of, the elements in the claims, as described herein.

GLOSSARY

An "isoalkane" is a hydrocarbon with the general formula $C_nH_{2n+2}$, n≥4 characterized by having at least one branch point, which means that the molecule contain at least one carbon atom bonded to three other carbon atoms and one hydrogen atom. The general formula for an isoalkane may be written as CHRR'R", wherein R, R' and R" are linear or branched alkyl groups For example:

*branch point

"Linear olefins" are unsaturated molecules with a linear hydrocarbon structure, and without any molecular branches.

"Alpha olefin" refers to any olefin having at least one terminal unconjungated carbon-carbon double bond.

"Base oil" refers to a hydrocarbon fluid to which other oils or substances are added to produce a lubricant.

"Lubricant" refers to substances (usually a fluid under operating conditions) introduced between two moving surfaces so as to reduce the friction and wear between them.

"Viscosity index" (VI) represents the temperature dependency of a lubricant, as determined by ASTM D2270-10 (E2011).

"Predominantly" refers to greater than 50 wt %, such as from greater than 50 wt % up to 100 wt %, in the context of this disclosure.

"Essentially" refers to from 90 wt % to 100 wt % in the context of this disclosure.

"API Base Oil Categories" are classifications of base oils that meet the different criteria shown in Table 1:

TABLE 1

| API Group | Sulfur, wt % | Saturates, wt % | Viscosity Index |
|---|---|---|---|
| I | >0.03 and/or | <90 | 80-119 |
| II | ≤0.03 and | ≥90 | 80-119 |
| III | ≤0.03 and | ≥90 | ≥120 |
| IV | All Polyalphaolefins (PAOs) | | |
| V | All base oils not included in Groups I-IV (naphthenics, non-PAO synthetics) | | |

"Group II+" is an unofficial, industry-established 'category' that is a subset of API Group II base oils that have a VI greater than 110, usually 112 to 119.

"Group III+" is another unofficial, industry-established 'category' that is a subset of API Group III base oils that have a VI greater than 130.

"Catalytic dewaxing", or "hydroisomerization dewaxing", refers to a process in which normal paraffins are isomerized to their more branched counterparts in the presence of hydrogen and over a catalyst.

"Kinematic viscosity" refers to the ratio of the dynamic viscosity to the density of an oil at the same temperature and pressure, as determined by ASTM D445-15.

"LHSV" means liquid hourly space velocity.

"Periodic Table" refers to the version of the IUPAC Periodic Table of the Elements dated Jun. 22, 2007, and the numbering scheme for the Periodic Table Groups is as described in Chemical And Engineering News, 63(5), 27 (1985).

"Bromine index" refers to the amount of bromine-reactive material in petroleum hydrocarbons and is a measure of trace amounts of unsaturates in these materials. Bromine index is reported in mg Br/100 g of sample.

"Acidic ionic liquid" refers to materials consisting entirely of ions, that can donate a proton or accept an electron pair in reactions, and that are liquid below 100° C.

DETAILED DESCRIPTION

The process comprises selecting an isoalkane feed and an olefin feed. The isoalkane feed contains at least one isoalkane and an olefin feed contains at least one linear olefin. The combined feeds (isoalkane and olefin) have a combined carbon number ($N_{alkane+olefin}$) that is from 20 to 60. For example, the isoalkane feed can have a feed isoalkane carbon number ($N_{alkane}$) greater than 6 and the olefin feed can have a linear olefin carbon number ($N_{olefin}$) greater than 9, such that the sum of the feed isoalkane carbon number and the linear olefin carbon number provides the combined carbon number from 20 to 60. In one embodiment, the isoalkane feed has a feed isoalkane carbon number ($N_{alkane}$) of 6 to 50. In one embodiment, the olefin feed has a linear olefin carbon number ($N_{olefin}$) of 10 to 43.

Isoalkane Feed

In one embodiment, the isoalkane feed is of biological origin. In one embodiment, the isoalkane feed can be produced by bacteria or yeast from fatty acids, fatty acid esters, or from free alkanes and alkenes. Examples of biomass that can be used to produce the isoalkane feed are animal oils and plant oils. In one embodiment, the isoalkane feed can be produced from animal oils or plant oils by reacting them, or their by-products, with hydrogen in a hydrodeoxygenation reactor, using a hydrogenation catalyst.

In one embodiment, the isoalkane feed comprise a mixture of isoalkanes. In one sub-embodiment the isoalkane feed comprises a mixture of isoalkanes that is prepared by oligomerizing C3-05 olefins to a mixture of oligomers and subsequently hydrogenating this mixture of oligomers to make the mixture of isoalkanes. Alkylation of isoalkanes prepared in this manner with linear alpha olefins has proved to be an effective method for making isoalkane alkylate base oils with very high VIs (i.e., VI>180) and having good cold flow properties (e.g., lower pour point, lower cold-cranking simulator apparent viscosity, or lower pumping viscosity by mini-rotary viscometer).

In one embodiment, the isoalkane feed is derived from a C10-C30 conjugated hydrocarbon terpene, such as farnesene, myrcene, ocimene, springene, or geranylfarnesene. One example of an isoalkane feed that can be derived from a C10-C30 conjugated hydrocarbon terpene is farnesane.

Farnesane in the shape of 2,6,10 trimethyldodecane has the following chemical structure:

Hydrogenation of farnesene isomer mixtures produces mixtures of trimethyldodecane isomers. In the context of this disclosure, the term farnesane is used to describe both the pure 2,6,10 trimethyl dodecane prepared from beta farnesene as well as isomer mixtures, including those prepared by hydrogenating farnesene isomer mixtures.

Olefin Feed Containing at Least One Linear Olefin

In one embodiment, the at least one linear olefin comprises an internal olefin. For example, the process can comprise isomerizing an alpha olefin to make the internal olefin.

In one embodiment, the at least one linear olefin is an alpha olefin.

In one embodiment, the at least one linear olefin is derived from one or more ketones. One method to produce the at least one linear olefin from ketones includes the steps of: a) converting an at least one dimeric ketone to an at least one alcohol, and b) dehydrating the at least one alcohol to make one or more corresponding olefins.

In one embodiment, the olefin feed is of biological origin. In one embodiment, the olefin feed can be produced by bacteria or yeast from fatty acids, fatty acid esters, or from free alkanes and alkenes. Examples of biomass that can be used to produce the olefin feed are animal oils, plant oils, and any carbon source that can be converted into one or more terpene compounds. In one embodiment, the olefin feed can be produced from animal oils or plant oils by partially hydrogenating them, or their by-products, with hydrogen in a hydro-deoxygenation reactor or in a hydrogenation reactor, using a hydrogenation catalyst. In one embodiment, the olefin feed comprises an acyclic C10-C30 terpene. In one embodiment, the olefin feed comprises a mono olefin derived from pure beta-farnesene. In one embodiment, the olefin feed comprises a mono olefin derived from a mixture of farnesene isomers.

Farnesene is a C15 poly-unsaturated and poly-branched terpene molecule that may be produced, for example, by fermentation of sugar. In one embodiment, the farnesene is of biological origin. In one embodiment, the farnesene is produced by a microorganism, including a bio-engineered microorganism. In one embodiment, the farnesene comprises a mixture of isomers. Farnesene exists in several isomeric forms. The isomer formed by fermentation is typically pure beta-farnesene but mixtures of farnesene isomers may be prepared by other methods from different starting materials. For instance, a mixture of farnesene isomers may in principle be prepared by trimerisation of isoprene. Farnesene isomer mixtures are available from common chemicals supplies. Farnesene is potentially available in significant volumes at a reasonable price. By hydrogenating the beta-farnesene, to the corresponding isoalkane, farnesane (2,6,10-trimethyldodecane) can be produced. It is also possible by selective hydrogenation to prepare the corresponding mono-olefin (2,6,10-trimethyldodecene). Processes for selective hydrogenation to produce the monoolefin farnesene are described in US Patent Pub. No. US20140221258A1.

In one embodiment, the olefin feed is a mixture of linear olefins obtained by isomerization of an alpha olefin or a mixture of olefins containing alpha olefins to increase the content of internal olefins in the olefin feed. Isomerizing the alpha-olefins in the olefin feed can improve the cold flow properties of the isoalkane alkylate base oil product, as illustrated by comparison of examples 1 and 2 in this disclosure.

In one embodiment, the process can additionally comprise passing the olefin feed over an olefin isomerization catalyst to shift a double bond to various different positions without structurally introducing branching in the at least one linear olefin prior to the alkylating. The double bond shift can improve the possibility to form an isoalkane alkylate base oil with a more diverse composition in the subsequent alkylation step and this favors better cold flow properties. Isomerization of an alpha olefin by double bond shift in the at least one linear olefin can improve the 1:1 selectivity in the subsequent alkylation, when the acidic alkylation catalyst comprises an acidic ionic liquid or HF. A similar phenomenon was observed in ionic liquid catalyzed isobutane alkylation where 2-butene reacts to form predominantly the 1:1 alkylate, isooctane, whereas 1-butene gives a mixture of 1:1, 2:1, 3:1, and heavier alkylates. When the alpha olefins show a marked tendency to form heavier alkylates, the corresponding internal linear olefins (beta-olefins, gamma-olefins, etc.) can have much less tendency to form heavier isoalkane alkylate base oils comprising more than one olefin unit per unit of isoalkane.

Alkylating

The process to make an isoalkane alkylate base oil comprises alkylating the isoalkane feed with the olefin feed in the presence of an acidic alkylation catalyst under alkylation conditions. The alkylating can be done at an alkylation temperature greater than −20° C., such as from −15° C. to 100° C., or from −10° C. to 50° C.

In one embodiment, the alkylating introduces branching into the isoalkane alkylate base oil at a central position. Introducing the branching into the alkylate base oil at a central position can increase the VI and/or reduce the pour point of the isoalkane alkylate base oil. The positioning of the branching in the isoalkane alkylate base oil can be determined by analyzing a sample of the isoalkane alkylate base oil using $^{13}C$ NMR (nuclear magnetic resonance).

In one embodiment, the acidic alkylation catalyst is selected from the group consisting of an acidic ionic liquid, a sulfuric acid, a hydrofluoric acid, a triflic acid, another Brønsted acid with a Hammet acidity function less than −10 ($H_0$<−10), an acidic zeolite, a sulfated zirconia, and a tungstated zirconia. The Hammett acidity function ($H_0$) is a measure of acidity that is used for very concentrated solutions of strong acids, including superacids. It was proposed by the physical organic chemist Louis Plack Hammett and is the best-known acidity function used to extend the measure of Brønsted-Lowry acidity beyond the dilute aqueous solutions for which the pH scale is useful.

Zeolites useful for alkylating isoalkanes include large pore zeolites such as for instance zeolite X and zeolite Y and zeolite beta, in their proton form or rare earth exchanged form.

In one embodiment, the acidic alkylation catalyst comprises an ionic liquid catalyst and a Brønsted acid. In this embodiment, the Brønsted acid acts as a promoter or co-catalyst. Examples of Brønsted acids are sulfuric acid, HCl, HBr, HF, phosphoric acid, HI, etc. Other strong acids that are proton donors can also be suitable Brønsted acids. In one embodiment, the Brønsted acid is produced internally within the process by the conversion of an alkyl halide into the corresponding hydrogen halide. In one embodiment the Brønsted acid is formed by a reaction of a Lewis acid component of an ionic liquid, such as chloroaluminate ions for instance reacting with a weakly acidic proton donor such as an alcohol or water to form HCl.

Acidic Ionic Liquid

Examples of acidic ionic liquid catalysts and their use for alkylation of paraffins with olefins are taught, for example, in U.S. Pat. Nos. 7,432,408 and 7,432,409, 7,285,698, and U.S. patent application Ser. No. 12/184,069, filed Jul. 31, 2008. In one embodiment, the acidic ionic liquid is a composite ionic liquid catalyst, wherein the cations come from a hydrohalide of an alkyl-containing amine or pyridine, and the anions are composite coordinate anions coming from two or more metal compounds.

The most common acidic ionic liquids are those prepared from organic-based cations and inorganic or organic anions. The acidic ionic liquid is composed of at least two components which form a complex. The acidic ionic liquid comprises a first component and a second component. The first component of the acidic ionic liquid will typically comprise a Lewis acid compound selected from components such as Lewis acid compounds of Group 13 metals, including aluminum halides, alkyl aluminum dihalides, gallium halide, and alkyl gallium halide (see the Periodic Table, which defines the elements that are Group 13 metals). Other Lewis acid compounds besides those of Group 13 metals may also be used. In one embodiment the first component is aluminum halide or alkyl aluminum dihalide. For example, aluminum trichloride ($AlCl_3$) may be used as the first component for preparing the ionic liquid catalyst. In one embodiment, the alkyl aluminum dihalides that can be used can have the general formula $Al_2X_4R_2$, where each X represents a halogen, selected for example from chlorine and bromine, each R represents a hydrocarbyl group comprising 1 to 12 atoms of carbon, aromatic or aliphatic, with a branched or a linear chain. Examples of alkyl aluminum dihalides include dichloromethylaluminum, dibromomethylaluminum, dichloroethylaluminum, dibromoethylaluminum, dichloro n-hexylaluminum, dichloroisobutylaluminum, either used separately or combined.

The second component making up the acidic ionic liquid can be an organic salt or mixture of salts. These salts may be characterized by the general formula Q+A−, wherein Q+ is an ammonium, phosphonium, boronium, oxonium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $Al_2Cl_7^-$, $Al_3Cl_{10}^-$, $GaCl_4^-$, $Ga_2Cl_7^-$, $Ga_3Cl_{10}^-$, $AsF_6^-$, $TaF_6^-$, $CuCl_2^-$, $FeCl_{13}^-$, $AlBr_4^-$, $Al_2Br_7^-$, $Al_3Br_{10}^-$, $SO_3CF_3^-$, and 3-sulfurtrioxyphenyl.

In one embodiment the second component is selected from those having quaternary ammonium halides containing one or more alkyl moieties having from about 1 to about 9 carbon atoms, such as, for example, trimethylammonium hydrochloride, methyltributylammonium, 1-butyl pyridinium, or alkyl substituted imidazolium halides, such as for example, 1-ethyl-3-methyl-imidazolium chloride.

In one embodiment, the acidic ionic liquid comprises a monovalent cation selected from the group consisting of a pyridinium ion, an imidazolium ion, a pyridazinium ion, a pyrazolium ion, an imidazolinium ion, a imidazolidinium ion, an ammonium ion, a phosphonium ion, and mixtures thereof. Examples of possible cations (Q+) include a butylethylimidazolium cation [beim], a butylmethylimidazolium cation [bmim], butyldimethylimidazolium cation [bmmim], decaethylimidazolium cation [dceim], a decamethylimidazolium cation [dcmim], a diethylimidazolium cation [eeim], dimethylimidazolium cation [mmim], an ethyl-2,4-dimethylimidazolium cation [e-2,4-mmim], an ethyldimethylimidazolium cation [emmim], an ethylimidazolium cation

[eim], an ethylmethylimidazolium [emim] cation, an ethylpropylimidazolium cation [epim], an ethoxyethylmethylimidazolium cation [etO-emim], an ethoxydimethylimidazolium cation [etO-mmim], a hexadecylmethylimidazolium cation [hexadmim], a heptylmethylimidazolium cation [hp-mim], a hexaethylimidazolium cation [hxeim], a hexamethylimidazolium cation [hxmim], a hexadimethylimidazolium cation [hxmmim], a methoxyethylmethylimidazolium cation [meO-emim], a methoxypropylmethylimidazolium cation [meO-prmim], a methylimidazolium cation [mim], dimethylimidazolium cation [mmim], a methylnonylimidazolium cation [mnim], a methylpropylimidazolium cation [mpim], an octadecylmethylimidazolium cation [octadmim], a hydroxylethylmethylimidazolium cation [OH-emim], a hydroxyloctylmethylimidazolium cation [OH-omim], a hydroxylpropylmethylimidazolium cation [OH-prmim], an octylmethylimidazolium cation [omim], an octyldimethylimidazolium cation [ommim], a phenylethylmethylimidazolium cation [ph-emim], a phenylmethylimidazolium cation [ph-mim], a phenyldimethylimidazolium cation [ph-mmim], a pentylmethylimidazolium cation [pnmim], a propylmethylimidazolium cation [prmim], a 1-butyl-2-methylpyridinium cation[1-b-2-mpy], 1-butyl-3-methylpyridinium cation[1-b-3-mpy], a butylmethylpyridinium [bmpy] cation, a 1-butyl-4-dimethylacetylpyridinium cation [1-b-4-DMApy], a 1-butyl-4-35 methylpyridinium cation[1-b-4-mpy], a 1-ethyl-2-methylpyridinium cation[1-e-2-mpy], a 1-ethyl-3-methylpyridinium cation[1-e-3-mpy], a 1-ethyl-4-dimethylacetylpyridinium cation[1-e-4-DMApy], a 1-ethyl-4-methylpyridinium cation[1-e-4-mpy], a 1-hexyl-5 4dimethylacetylpyridinium cation[1-hx-4-DMApy], a 1-hexyl-4-methylpyridinium cation[1-hx-4-mpy], a 1-octyl-3-methylpyridinium cation[1-o-3-mpy], a 1-octyl-4-methylpyridinium cation[1-o-4-mp y], a 1-propyl-3-methylpyridinium cation[1-pr-3-mpy], a 1-propyl-4-methylpyridinium cation[1-pr-4-mpy], a butylpyridinium cation [bpy], an ethylpyridinium cation [epy], a heptylpyridinium cation [hppy], a hexylpyridinium cation [hxpy], a hydroxypropylpyridinium cation [OH-prpy], an octylpyridinium cation [opy], a pentylpyridinium cation [pnpy], a propylpyridinium cation [prpy], a butylmethylpyrrolidinium cation [bmpyr], a butylpyrrolidinium cation [bpyr], a hexylmethylpyrrolidinium cation [hxmpyr], a hexylpyrrolidinium cation [hxpyr], an octylmethylpyrrolidinium cation [ompyr], an octylpyrrolidinium cation [opyr], a propylmethylpyrrolidinium cation [prmpyr], a butylammonium cation [b-N], a tributylammonium cation [bbb-N], a tetrabutylammonium cation [bbbb-N], a butylethyldimethylammonium cation [bemm-N], a butyltrimethylammonium cation [bmmm-N], a N,N,N-trimethylethanolammonium cation [choline], an ethylammonium cation [e-N], a diethylammonium cation Fee-NI, a tetraethylammonium cation [eeee-N], a tetraheptylammonium cation [hphphphp-N], a tetrahexylammonium cation [hxhxhxhx-N], a methylammonium cation [m-N], a dimethylammonium cation [mm-N], a tetramethylammonium cation [mmmm-N], an ammonium cation [N], a butyldimethylethanolammonium cation [OHe-bmm-N], a dimethylethanolammonium cation [OHe-mm-N], an ethanolammonium cation [OHe—N], an ethyldimethylethanolammonium cation [OHe-emm-N], a tetrapentylammonium cation [pnpnpnpn-N], a tetrapropylammonium cation [prprprpr-N], a tetrabutylphosphonium cation [bbbb-P], a tributyloctylphosphonium cation [bbbo-P], or combinations thereof.

In one embodiment, the second component is selected from those having quaternary phosphonium halides containing one or more alkyl moieties having from 1 to 12 carbon atoms, such as, for example, trialkyphosphonium hydrochloride, tetraalkylphosphonium chlorides, and methyltrialkyphosphonium halide.

In one embodiment, the acidic ionic liquid comprises an unsubstituted or partly alkylated ammonium ion.

In one embodiment, the acidic ionic liquid is chloroaluminate or a bromoaluminate. In one embodiment the acidic ionic liquid is a quaternary ammonium chloroaluminate ionic liquid having the general formula RR'R"NH+Al$_2$Cl$_7^-$, wherein R, R', and R" are alkyl groups containing 1 to 12 carbons. Examples of quaternary ammonium chloroaluminate ionic liquids are an N-alkyl-pyridinium chloroaluminate, an N-alkyl-alkylpyridinium chloroaluminate, a pyridinium hydrogen chloroaluminate, an alkyl pyridinium hydrogen chloroaluminate, a di alkyl-imidazolium chloroaluminate, a tetra-alkyl-ammonium chloroaluminate, a tri-alkyl-ammonium hydrogen chloroaluminate, or a mixture thereof.

The presence of the first component should give the acidic ionic liquid a Lewis or Franklin acidic character. Generally, the greater the mole ratio of the first component to the second component, the greater is the acidity of the acidic ionic liquid.

For example, a typical reaction mixture to prepare n-butyl pyridinium chloroaluminate ionic liquid is shown below:

In one embodiment, the acidic ionic liquid utilizes a co-catalyst to provide enhanced or improved alkylation activity. Examples of co-catalysts include alkyl halide or hydrogen halide. A co-catalyst can comprise, for example, anhydrous HCl or organic chloride (see, e.g., U.S. Pat. No. 7,495,144 to Elomari, and U.S. Pat. No. 7,531,707 to Harris et al.). When organic chloride is used as the co-catalyst with the acidic ionic liquid, HCl may be formed in situ in the apparatus either during the alkylating or during post-processing of the output of the alkylating. In one embodiment, the alkylating with the acidic ionic liquid is conducted in the presence of a hydrogen halide, e.g., HCl.

The alkyl halides that may be used include alkyl bromides, alkyl chlorides and alkyl iodides. Such alkyl halides include but are not limited to isopentyl halides, isobutyl halides, t-butyl halides, n-butyl halides, propyl halides, and ethyl halides. Alkyl chloride versions of these alkyl halides can be preferable when chloroaluminate ionic liquids are used. Other alkyl chlorides or alkyl halides having from 1 to 8 carbon atoms can be also used. The alkyl halides may be used alone or in combination.

When used, the alkyl halide or hydrogen halide co-catalysts are used in catalytic amounts. In one embodiment, the amounts of the alkyl halides or hydrogen halide should be kept at low concentrations and not exceed the molar concentration of the AlCl$_3$ in the acidic ionic liquid. For example, the amounts of the alkyl halides or hydrogen halide used may range from 0.05 mol %-100 mol % of the Lewis acid AlCl$_3$ in the acidic ionic liquid in order to keep the acidity of the acidic ionic liquid catalyst at the desired performing capacity.

In one embodiment, the acidic alkylation catalyst comprises an ionic liquid catalyst and a BrØnsted acid. In this embodiment, the BrØnsted acid acts as a promoter or co-catalyst. Examples of BrØnsted acids are sulfuric acid, HCl, HBr, HF, phosphoric acid, HI, etc. Other strong acids that are proton donors can also be suitable BrØnsted acids. In one embodiment, the BrØnsted acid is produced internally within the process by the conversion of an alkyl halide into the corresponding hydrogen halide.

In one embodiment, the process can additionally comprise recycling an excess of the isoalkane feed to the alkylating. For example, the process can include distilling out an excess isoalkane after the alkylating and then recycling the excess isoalkane to the alkylating.

In one embodiment, the process can additionally comprise neutralizing a residual acidic alkylation catalyst in the isoalkane alkylate base oil.

Isoalkane Alkylate Base Oil

In one embodiment, the isoalkane alkylate base oil has a VI higher than 90, a kinematic viscosity at 100° C. from 2 to 30 mm$^2$/s, a pour point less than 0° C., and a bromine index less than 2000 mg Br/100 g. Pour point can be determined by ASTM D5950-14, or by an equivalent test method.

In one embodiment, the isoalkane alkylate base oil comprises from zero to less than 5 wt % linear alkanes.

In one embodiment, the isoalkane alkylate base oil comprises from zero to less than 100 wppm aromatics. In a sub-embodiment, the isoalkane alkylate base oil can comprise from zero to less than 10 ppb aromatics.

In one embodiment, the isoalkane alkylate base oil comprises less from zero to less than 25 wppm sulfur. In a sub-embodiment, the isoalkane alkylate base oil can comprise from zero to less than 10 ppb sulfur.

In one embodiment the VI is from 91 to 200. In one embodiment the VI is higher than 120. In different embodiments, the isoalkane alkylate base oil is an API Group II, an API Group II+, an API Group III, or an API Group III+ base oil.

In one embodiment, the isoalkane alkylate base oil comprises a mixture of isoalkanes, and in a sub-embodiment the isoalkane alkylate base oil can consist predominantly of a mixture of isoalkanes in the base oil boiling range. The base oil boiling range is defined herein as a boiling point range between 550° F. (287.8° C.) and 1292° F. (700° C.), where in the lower value is the T5 boiling point and the upper value is the T95 boiling point. Boiling range is measured by simulated distillation according to ASTM D6352-15, or an equivalent test method. An equivalent test method refers to any analytical method which gives substantially the same results as the standard method. T5 relates to the temperature at which 5 weight percent of the isoalkane base oil has a lower boiling point. T95 refers to the temperature at which 95 weight percent of the isoalkane alkylate base oil has a lower boiling point. The isoalkanes in the base oil boiling range are generally hydrocarbons with 18 to 60 carbon atoms.

In one embodiment, the isoalkane alkylate base oil comprises localized branching introduced partially from the isoalkane feed and partially from the alkylating.

The pour point, and other cold flow properties, of the isoalkane alkylate base oil can be excellent. For example, the pour point can be less than or equal to −15° C., less than −24° C., or even less than −50° C.

In one embodiment, the isoalkane alkylate base oil is essentially free of olefins and aromatics and consists predominantly of long carbon chain molecules having a straight chain of no less than 12 carbon atoms and having at least one branch towards the middle of the straight chain, and characterized by:

a) the isoalkane base oil contains less than 10 wt % n-alkanes, less than 0.1 wt % olefinic hydrocarbons, and less than 0.1 wt % aromatic hydrocarbons;
b) the at least one branch is a branched alkyl group containing 4 or more carbon atoms; and
c) the long carbon chain molecules have two terminal linear unbranched alkyl groups each containing at least 4 carbons. In a sub-embodiment, the branched alkyl group containing 4 or more carbon atoms can be an isobutyl group, an isohexyl group, a tertiary butyl group, or a poly-branched nonyl group. In a sub-embodiment, the two terminal linear unbranched alkyl groups each containing at least 4 carbons can be n-butyl-, n-pentyl-, or $nC_nH_{2n+1-}$, where n is greater than or equal to 4.

Bromine Index

In one embodiment, the isoalkane alkylate base oil has a bromine index from less than 100 to less than 2000 mg Br/100 g. In one embodiment, the isoalkane alkylate base oil has a bromine index less than 500 mg Br/100 g. The bromine index less than 2000 mg Br/100 g, or even less than 200 mg Br/100 g can be obtained prior to any subsequent hydrogenation.

Bromine index can be determined by proton Nuclear Magnetic Resonance (NMR). Proton NMR is generally taught in https://en.wikipedia.org/wiki/Ploton_nuclear_magnetic_resonance.

The following assumptions are made for the Bromine index determinations in test samples of alkylate base oil:
1) Residual olefins in the test sample are represented by the formula: R1R2C=CHR3, so that one vinylic hydrogen represents an olefin group.
2) The average carbon in the test sample caries two protons and thus may be represented by an average molecular wt of 14.0268 g/mole
3) All proton resonances in the range 0.5-0.95 represent methyl groups (3 protons per carbon)
4) All proton resonances in the range 0.95-1.40 ppm represent $CH_2$ groups (2 protons per carbon)
5) All proton resonances in the range 1.4-2.1 ppm represent CH groups (1 proton per carbon)
6) All proton resonances in the range 4-6 ppm represent RR'C=CHR" groups (0.5 proton per carbon or one per double bond).
7) One double bond reacts with one equivalent of bromine, i.e., one mole of olefin reacts with one mole of dibromine ($Br_2$, MW=159.8 g/mole)

Integrals in the acquired proton NMR spectrum are represented by I("group"), e.g., the integral of a methyl group is I(CH3) and the integral of an olefin group is I(RR'C=CHR").

Bromine number is defined as the amount of bromine (in g $Br_2$) needed to titrate all the olefins in 100 g of the test sample. Bromine index=1000*bromine number.

The bromine index is calculated from the proton NMR integrals with the following formula: Bromine index=1000*100*(159.8/14.0268)*I(RR'C+CHR")/{0.3333*I(CH3)+0.5*I(CH2)+I(CH)+2*I(RR'C=CHR")}.

The absence of any proton resonances in the NMR spectrum is interpreted as a bromine index <100, based on the sensitivity of the proton NMR spectrometer that is used.

In one embodiment, the isoalkane alkylate base oil has a bromine index less than 100.

$^{13}$C NMR

We have discovered that proton decoupled $^{13}$C NMR offers the opportunity to identify long unbranched terminal alkyl chains and to quantify them relative to other parts of the molecules and thus allowing to confirm the structure of an alkylate base oil in which an alkyl group is placed towards the center of a long straight chain molecule $^{13}$C NMR is an effective method for identifying the environment of carbon atoms in an organic molecule. In comparison to $^1$H NMR the $^{13}$C NMR covers a far broader range and the $^{13}$C chemical shift may thus be a more useful tool in the analysis of complex organic materials such as alkylate base oils.

Hydrocarbon oils such as the materials used for base oil are typically very complex mixtures of predominantly saturated hydrocarbons and the $^1$H NMR spectra of these materials are typically not very informative. In comparison to $^1$H NMR, the $^{13}$C NMR is spread out over s far broader chemical shift range and $^{13}$C NMR could thus be more useful tool for characterizing base oils, even the proton decoupled $^{13}$C NMR spectrum is typically complicated. However, we have discovered that surprisingly when the base oil is essentially saturated, the $^{13}$C NMR spectrum can be used to identify the existence of long linear terminal alkyl chains in the molecules.

In an unbranched chain of carbon atoms ending in a terminal methyl group of the general formula: $CH_3$—$CH_2$—$CH_2$—$CH_2$—$(CH_2$—$)_n$— the $^{13}$C NMR chemical shifts of the first 4 carbons (C1-C4 with the terminal methyl being C1) in a long unbranched chain are distinct and well defined and their existence in the $^{13}$C NMR spectrum may therefore be used as probe for long unbranched terminal carbon chains. The subsequent carbons in a linear chain (C5+) all show up in the same narrow resonance range. Labelled from the terminal alkyl the chemical shifts relative to TMS for a long unbranched terminal alkyl chains are as follows:

C1: 13.9-14.2 ppm, C2: 22.6-22.8 ppm, C3: 31.9-32.05 ppm, C4: 29.35-29.45 ppm, C5+: 29.6-29.8 ppm.

Since a branch in the carbon chain impacts the chemical shifts of the neighboring 3 carbons the existence of the C1-O5+ series resonances at a 1:1:1:1:1 integral intensity is indicative of terminal unbranched 8 carbon chains. Additional —$CH_2$— groups in the chain show up as an increased integral in the C5+ resonance range. Shorter carbon chains do not exhibit the C5+ resonances but may still show the resonances anticipated for the first carbon(s) in the long chain range series shown above. For instance, a linear terminal 5-carbon alkyl group on a branched carbon will exhibit the C1 and C2 resonances in the ranges for long chain terminal alkyl groups but the C3, C4 and C5 resonances will typically be shifted out of the long chain resonance ranges given above.

For the application of this method it is important that the integrals of the individual resonances represent the relative amounts of the carbon they represent. Therefore, when acquiring the spectra care is taken to allow sufficient relaxation delay to allow the individual carbons to return to their natural state between the pulses. Failure to do this would result in some resonances giving smaller integrals than would be anticipated from their abundance. Fortunately, since protons attached to a carbon nucleus helps it relax in the magnetic field this is mostly an issue that carbons not carrying any proton substituents and the carbon resonances used in this method all carry at least 2 hydrogen atoms.

The $^{13}$C NMR method described above is most useful to identify and quantify the existence of long (C8+) linear alkyl groups in the molecules of hydrocarbon mixtures in the base oil and heavy diesel boiling point ranges.

Provided we have a rough idea of the total carbon number in the average molecule in a sample this $^{13}$C NMR method can be used to evaluate if an oil composed of substantially linear molecules with a few branches has these branches in a central part of the main chain or towards the end. If it is towards the end we only expect one long terminal alkyl chain per molecule whereas if the branching is in the center of the chain there will be two long chain terminal alkyl chains.

Table 2 contains proton decoupled $^{13}$C NMR spectroscopic data that illustrates the new method.

TABLE 2

| Compound | Normalized Integrals | | | | | |
| --- | --- | --- | --- | --- | --- | --- |
| | C1 | C2 | C3 | C4 | C5+ | Other |
| n-Octane | 1.0 | 1.0 | 1.0 | 1.0 | 0.0 | 0.0 |
| n-Dodecane | 1.0 | 1.0 | 1.0 | 1.0 | 2.1 | 0.0 |
| n-Hexadecane | 1.0 | 1.0 | 1.1 | 1.0 | 4.3 | 0.0 |
| 1-Tetradecene | 1.0 | 1.0 | 1.0 | 0.9 | 3.8 | 5.3 |
| 11-Tricosene | 1.0 | 1.0 | 1.1 | 1.0 | 3.8 | 4.2 |
| 2,2,4-Trimethylpentane | 0.0 | 0.0 | 0.0 | 0.0 | 0.0 | 8.0 |
| Hydrogenated propylene oligomer | 0.0 | 0.2 | 0.0 | 0.0 | 1.0 | 64.8 |
| 1-C14= + 2MePent alkylate | 1.0 | 1.0 | 0.8 | 0.8 | 3.7 | 2.5 |
| n-C14= isomer mixture + 2MePent alkylate | 1.0 | 1.3 | 0.8 | 1.1 | 2.2 | 10.6 |
| 11-Tricosene + farnesane | 1.0 | 1.8 | 1.0 | 1.0 | 3.5 | 8.0 |
| 11-Tricosene + 2MePent | 1.0 | 1.0 | 1.1 | 1.0 | 3.1 | 3.0 |
| 11-tricosene + mixed C6, C9 and C12 isoalkanes | 1.0 | 1.2 | 1.0 | 1.2 | 4.0 | 5.6 |

In this $^{13}$C NMR method, C1 refers to 13.9-14.2 ppm, C2 refers to 22.6-22.8 ppm, C3 refers to 31.9-32.05 ppm, C4 refers to 29.35-29.45 ppm, and C5+ refers to 29.6-29.8 ppm, where C1 represents the terminal methyl group carbon, C2 represents the methylene group next to the terminal methyl group carbon, and so forth. Where available, the integrals are normalized relative to the integral of the terminal methyl resonance (i.e., C1 around 14.1 ppm) in such a way that the integrals of other resonances in the spectra are measured relative to this resonance. For the spectra of compounds not containing any long terminal alkyls groups (e.g., isooctane or hydrogenated propylene oligomer oil) the absolute values of the integrals are arbitrary.

The three n-alkanes (n-octane, n-dodecane, and n-hexadecane) all exhibit relative resonances consistent with two terminal alkyl groups of varying length. n-Octane is missing the C5+ integrals because the molecule is too short to have any carbon in a chain that is more than 4 carbons from the nearest terminal carbon. Since these three n-alkanes all have two terminal alkyl groups and thus two terminal methyl groups on long chain alkyl groups. Consequently, normalized integral represents two carbon atoms for each unit in the normalized integrals; n-octane has 0 C5+, n-dodecane has 4 C5+, and n-hexadecane has 8 C5+, so we would expect the C5+ intensities to be 0, 2, and 4 respectively, while the experimental data shows 0, 2.1 and 4.3. The deviation reflects the uncertainty in the method caused by varying relaxation times. While this uncertainty may impact the accuracy of an estimate of chain length of very long chain terminal alkyl groups it is insignificant relative to the estimated abundance of terminal alkyl groups.

For the 1-tetradecene data, the normalized integral represents 1 carbon per unit and again the normalized integrals for C1-C5+ are consistent with the molecule n-$C_{12}H_{25}CH$=$CH_2$ containing 1 terminal long chain alkyl group. For the 11-tricosene data, the normalized integrals are consistent with the normalized integrals representing two carbons per unit and are consistent with two long chain terminal alkyl groups in the molecule $C_{11}H_{23}CH$=$CHC_{10}H_{21}$.

2,2,4 Trimethylpentane (isooctane) and the hydrogenated propylene oligomer oil (heavy base oil to bright stock range) are included in Table 2 as examples of two materials that do not contain long chain terminal alkyl groups. The $^{13}$C NMR spectra of 2,2,4-Trimethylpentane and hydrogenated propylene oligomer consequently do not consistently contain resonances in all 5 ranges expected for long chain terminal alkyl groups and neither contains resonances in the range expected for the 13.9-14.1 ppm range where the methyl carbon of a long chain alkyl group would be expected. It is in particular noteworthy that, while the hydrogenated propylene oligomer oil spectrum is quite complicated and (not surprisingly) some resonances show up within some of the ranges associated with terminal alkyl groups, more than 98% of the integral area in the $^{13}$C NMR of this base oil is outside of these ranges.

The remaining data in Table 2 represent data for various alkylation products made by ionic liquid catalyzed alkylation.

Table 2 contains $^{13}$C NMR data for isoalkane alkylate base oils made by alkylation of 2-methylpentane (isohexane) with 1-tetradecene and with an n-tetradecene isomer mixture respectively. The preparation of these two samples are further described in Examples 1 and 2, herein. The n-tetradecene isomer mixture may be prepared by isomerization of the alfa olefin (NAO)1-tetradecene through catalytic double bond shift. It is important to note that the olefin isomerization we used did not introduce any structural changes in form of branching in the olefin—it only shifted the double bond from the terminal position to various internal positions The 11-tricosene alkylate data all confirm that the alkylation in these very long molecules happens predominantly in the central part of the chain leaving a long straight backbone with two long chain alkyl ends.

The data presented herein show that it is possible to synthesize a unique class of isoalkane alkylate base oils characterized by that the alkylate branching is introduced in the molecule in a central position such that the $^{13}$C NMR data show intensity in the long chain terminal alkyl group ranges described above corresponding to two long chain terminal alkyl groups per molecule.

In one embodiment, more than 25% of the total $^{13}$C NMR integrals fall within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+(29.6-29.8 ppm). In one embodiment, more than 50% of the total $^{13}$C NMR integrals fall within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+(29.6-29.8 ppm). For example, in one embodiment, the total $^{13}$C NMR integrals falling with $^{13}$C NMR resonances in ranges for linear long chain alkyl groups can be from 26% to 80%.

Finished Lubricant

In one embodiment, the process additionally comprises blending the isoalkane alkylate base oil with at least one additive to make a finished lubricant. A wide variety of high quality finished lubricants can be made by blending the isoalkane alkylate base oil with at least one additive selected from the group consisting of antioxidants, detergents, anti-wear agents, metal deactivators, corrosion inhibitors, rust inhibitors, friction modifiers, anti-foaming agents, viscosity index improvers, demulsifying agents, emulsifying agents, tackifiers, complexing agents, extreme pressure additives, pour point depressants, and combinations thereof; wherein selection of the at least one additive is directed largely by the end-use of the finished lubricant being made, wherein said finished lubricant can be of a type selected from the group consisting of engine oils, greases, heavy duty motor oils, passenger car motor oils, transmission and torque fluids, natural gas engine oils, marine lubricants, railroad lubricants, aviation lubricants, food processing lubricants, paper and forest products, metalworking fluids, gear lubricants, compressor lubricants, turbine oils, hydraulic oils, heat transfer oils, barrier fluids, and other industrial products. In one embodiment, the alkylate base oil can be blended with at least one additive to make a multi-grade engine oil.

EXAMPLES

Example 1: Alkylation of 2-Methylpentane with 1-Tetradecene 400 ml of 2-methyl pentane (isohexane, $C_6H_{14}$) was combined with 40 ml n-butylpyridinium heptachlorodialuminate ionic liquid in a mechanically stirred 2 liter reaction flask under inert atmosphere and cooled to 3-5° C. on an ice bath. A mixture of 50 ml (37.4 g) 1-tetradecene ($C_{14}H_{28}$), 50 ml 2-methyl pentane and 0.5 ml t-butyl chloride was slowly added over a period of 47 minutes and the agitation was continued for an additional 6 minutes before the agitation was stopped and the phases was allowed to separate. The hydrocarbon phase was decanted off. About 80% of this crude hydrocarbon product was cleared by centrifugation and filtered through anhydrous $MgSO_4$. The resulting solution was concentrated on a rotary evaporator (RotoVap) to remove volatile components leaving 35 g of an isoalkane alkylate base oil with the properties illustrated in Table 3.

TABLE 3

| | |
|---|---|
| Viscosity Index | 191 |
| Kinematic Viscosity at 100° C., mm$^2$/s | 7.705 |
| Kinematic Viscosity at 40° C., mm$^2$/s | 36.06 |
| Pour Point, ° C. | −20 |
| Cloud Point, ° C. | −15 |
| Bromine Index, mg Br/100 g estimated from NMR | <100 |

The proton NMR of the product confirmed that the isoalkane alkylate base oil was completely saturated and contained no vinylic protons. The proton NMR confirmed that the isoalkane alkylate base oil was an alkylate and not an oligomer. This example demonstrated the process of this invention using a combined carbon number of the isoalkane feed and the olefin feed of 20.

In one embodiment, the kinematic viscosity of the isoalkane alkylate base oil is higher than would be expected from a C20 isoalkane. This is because in alkylation of isoalkanes with alpha olefins the aluminum chloride-based ionic liquid catalysis can result in formation of products incorporating more than one olefin unit and thus forming an alkylate product heavier that the simple 1:1 alkylates.

Example 2: Alkylation of 2-Methylpentane with a Mixture of Linear Tetradecene Isomers 400 ml of 2-methyl pentane (isohexane) was combined with 40 ml n-butylpyridinium heptachlorodialuminate ionic liquid in a mechanically stirred 2 liter reaction flask under inert atmosphere and cooled to 3-5° C. on an ice bath. A mixture of 50 ml (37.4 g) tetradecene (linear isomer blend prepared from 1-tetradecene by double bond shift) 50 ml 2-methyl pentane and 0.5 ml t-butyl chloride was slowly added over a period of 34 minutes and the agitation was continued for an additional 10 minutes before the agitation was stopped and the phases was allowed to separate. The hydrocarbon phase was decanted off, washed with water, then washed with aqueous sodium bicarbonate, and then filtered through anhydrous MgSO$_4$ to produce a clear colorless solution. This solution was concentrated on a RotoVap to remove volatile components, leaving 54.3 g of an isoalkane alkylate base oil with the properties shown in Table 4.

TABLE 4

| Viscosity Index | 123 |
| Kinematic Viscosity at 100° C., mm$^2$/s | 2.176 |
| Kinematic Viscosity at 40° C., mm$^2$/s | 6.921 |
| Pour Point, ° C. | −46 |
| Cloud Point, ° C. | −36 |
| Bromine Index, mg Br/100 g estimated from NMR | <100 |

As in Example 1, the proton NMR of the product confirmed that the isoalkane alkylate base oil was completely saturated and contained no vinylic protons. The proton NMR confirmed that the isoalkane alkylate base oil was an alkylate and not an oligomer.

This example also demonstrated the process of this invention using a combined carbon number of the isoalkane feed and the olefin feed of 20. In this example the kinematic viscosity of the isoalkane alkylate base oil was shifted lower (i.e., from 7.705 to 2.176 mm$^2$/s at 100° C.) by using an olefin feed comprising a linear isomer blend prepared from an alpha olefin by double bond shift. The cloud point and pour point were also shifted to lower values. Both of these changes are consistent with an increased selectivity in the ionic liquid catalyzed alkylation reaction towards the 1:1 alkylates.

Figure 1:
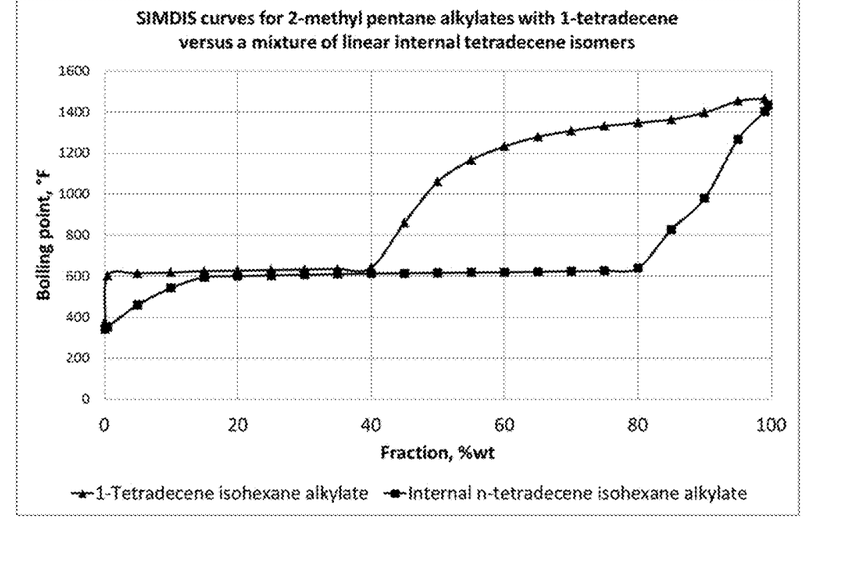
FIG. 1 is a graph of SIMDIS curves of two of the examples in this disclosure. One line shows the products of 1-tetradecene (example 1) and the other line shows the products of isomerized linear tetradecene (example 2).

The effect on the alkylate product of isomerizing the alpha olefin to an internal olefin is also illustrated in the graphic presentation in FIG. 1.

$^{13}$C NMR normalized integrals for the isoalkane alkylate base oils prepared in Examples 1 and 2 are included in Table 2, provided earlier. The $^{13}$C NMR data for 1-tetradenene and isomerized n-tetradecene alkylation revealed some surprises. Intuitively, one would expect that using internal liner olefins instead of the 1-olefin would give more material with two long chain terminal alkyl group by increasing the tendency for introducing the branching of the molecule towards the center of the chain but the data show that the effect of the double bond shift in the feed olefin is far more complex.

The data for the 1-tetradecene alkylation show that there is very little product outside the terminal alkyl ranges. Since we know from other product data that the average product molecule made in this alkylation contained more than one olefin unit per isohexane unit this is consistent with other data provided that structural isomerization of the linear C14 chain is limited. However, the intensity of, in particular, the C1 and C2 long chain alkyl resonances compared to the total integrals suggest that the molecule contains closer to two terminal long chain alkyl groups than to one suggesting that the i-C6 alkyl group is attached towards the center of the C14 chain.

The data for the alkylate made from isomerized tetradecene show that more than 60% of the integrals fall outside the terminal alkyl group ranges and the intensity of the terminal alkyl resonances average to only about one long chain terminal alkyl group per molecule. This suggests that the double bond shift of the olefin aside from improving the 1:1 alkane to olefin ratio in the alkylate products has been to cause the alkylation to be accompanied by structural isomerization and introduction of additional branching in the C14 chain.

In Example 1, 74.5% of the total $^{13}$C NMR integrals fall within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+ (29.6-29.8 ppm).

In Example 2, 37.6% of the total $^{13}$C NMR integrals fall within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+ (29.6-29.8 ppm).

Example 3: Ketonization of Lauric Acid (Dodecanoic Acid, Fatty Acid) to 12-Tricosanone (Laurone, Ketone) Using an Alumina Catalyst The ketonization of lauric acid (dodecanoic acid) to 12-tricosanone (laurone, ketone) was catalyzed by an alumina catalyst operated in a fixed bed continuously fed reactor at ambient pressure, at a temperature range of 770 to 840° C., and with a feed rate that gave a liquid hourly space velocity (LHSV) of 0.62 to 0.64 h$^{-1}$. The conversion of lauric acid to laurone was calculated based on the composition of the product, as determined by gas chromatography (GC) using a flame ionization detector (FID).

The freshly loaded new alumina catalyst was calcined in the reactor at 482° C. (900° F.) with a stream of dry nitrogen (2 volumes of nitrogen per volume of catalyst per minute) for 2 hours. Then the temperature was lowered to 410° C. (770° F.), the nitrogen stream was stopped, and the lauric acid feed was introduced into the reactor. Product composition analysis showed that the fresh catalyst operating at 410° C., LHSV=0.62 to 0.64 h$^{-1}$, gave a lauric acid conversion of 62 to 66 wt %.

The reactor effluent was split in a continuously operated stripping column from which the laurone product was isolated as a bottom cut containing less than 1 wt % unconverted lauric acid. The unconverted fatty acid (lauric acid) taken overhead from the stripping column was recycled to the reactor, except for a small amount (<5 wt % relative to the fresh fatty acid feed stock) of light cracked products. The light cracked products were predominantly n-alkanes and linear alpha olefins. The light cracked products were withdrawn from the stripping column as the only by-product stream.

Example 4: Hydrogenation of 12-Tricosanone to 12-Tricosanol Over Ruthenium/Carbon Catalyst 12-tricosanone (laurone, ketone) prepared as described in Example 3 was hydrogenated over a carbon supported ruthenium catalyst to make the corresponding alcohol, 12-tricosanol as described here.

800 g of the 12-tricosanone was loaded into a 1 liter stirred batch autoclave together with 1 g of a catalyst having 5 wt % ruthenium on carbon. The mixture of the 12-tricosanone and catalyst was put under 1500 psig (10342 kPa) hydrogen pressure, stirred, and heated to 200° C. Hydrogen was added as it was consumed in order to maintain the hydrogen pressure in the reactor during the run. After 23 hours the reaction was stopped and the reactor contents withdrawn and filtered to yield the 12-tricosanol product. Proton nuclear magnetic resonance (NMR) indicated that the conversion was about 89 wt % and the selectivity to the alcohol was greater than 90 wt %, with the corresponding alkane, tricosane, being the only by-product.

Example 5: Hydrogenation of 12-Tricosanone to 12-Tricosanol Over Ruthenium/Tin/Carbon Catalyst 2185 g of 12-tricosanone prepared as described in Example 3 was loaded into a 1 gallon (3.785 liters) stirred autoclave with 3 g of a catalyst comprising 5 wt % ruthenium on a tin promoted carbon support. The mixture of the 12-tricosanone and catalyst was put under 1500 psig (10342 kPa) hydrogen pressure, stirred, and heated to 200° C. Hydrogen was added as it was consumed in order to maintain the hydrogen pressure in the reactor during the run. After 36 hours the reaction was stopped and the reactor contents withdrawn and filtered to yield the 12-tricosanol product. Proton nuclear magnetic resonance (NMR) indicated that the conversion was about 93 wt % and the selectivity to 12-tricosanol was about 95 wt %. Later analysis of the olefin isolated by dehydration of the 12-tricosanol product (see Example 7) showed that the product contained less than 2 wt % alkane, indicating greater than 98 wt % selectivity in this hydrogenation step.

Example 6: Dehydration of 12-Tricosanol to a Mixture of Predominantly Cis, Trans-11-Tricosene Over an Alumina Catalyst The 12-tricosanol, made as described in Example 5, was used as prepared without further purification. The 12-tricosanol was fed at a LHSV of 0.4-0.53 hr$^{-1}$ to a fixed bed reactor containing 50 ml freshly regenerated alumina catalyst of the same kind used for the ketonization described in Example 1. The regeneration of the alumina catalyst was done by contacting the catalyst with an oxidizing gas to remove coke and further contacting the catalyst with steam, as described in a U.S. patent application Ser. No. 14/540,723, filed Nov. 13, 2014.

GC and NMR analysis of the product withdrawn from the fixed bed reactor, after ejection of water, showed a 12-tricosanol conversion of 87 to 90 wt %, and near quantitative (about 99 wt %) selectivity to a mixture of cis and trans 11-tricosene, with only traces of other olefin isomers. The GC and NMR analysis showed the presence of 2 wt % tricosane relative to the combined tricosane and tricosene carried over from the hydrogenation step described in Example 5.

Example 7: Hydrogenation of 12-Tricosanone to 12-Tricosanol Over Pt/Carbon Hydrogenation Catalyst 12-tricosanone (laurone, ketone) prepared as described in Example 3 was hydrogenated over a carbon supported platinum catalyst to make the corresponding alcohol, 12-tricosanol as described here.

The 12-tricosanone was introduced as a liquid flow (4.1-4.4 g/hr, 12-13 mmoles/hr) together with hydrogen (100 Nml/min, 250 mmoles/hr) to a fixed reactor holding 7 ml of a catalyst comprising 0.5 wt % platinum on carbon. The amount of the catalyst was 3.5 g, and the catalyst had a particle size of 0.3 to 1 mm. The pressure was held at 1500 psig (10342 kPa). The liquid products were collected after the reaction and analyzed by GC. The liquid product stream contained three components: 1) unconverted 12-tricosanone, 2) 12-tricosanol, and 3) the corresponding n-alkane, n-tricosane. The n-tricosane was present only in trace amounts.

At a reaction temperature from 450 to 470° F. (232.2 to 243.3° C.), the GC analysis of the product showed a conversion of 12-tricosanone of 80 to 87 wt %, and a selectivity to 12-tricosanol of 98.9 to 99.4 wt %. The remaining 0.6 to 1.1 wt % of the product was n-tricosane formed by hydrodeoxygenation of the alcohol.

Example 8: Isolation of Tricosene from Crude Tricosene Product

Several efficient methods can be used for separation of tricosene from unconverted 12-tricosanol and 12-tricosanone. One method exploited the far higher solubility of the olefin in light alkane solvents at low temperature. It was possible to perform the separation of the tricosene by dissolving the mixture of tricosene, tricosanol, and tricosanone in hexane and cooling the dissolved mixture to −20° C. to precipitate out essentially all of the unconverted tricosanol and tricocanone. The solid precipitates were removed by filtration and after subsequent evaporation of the hexane solvent, a purified tricosene product containing 0.02 wt % tricosanol and 0.9 wt % tricosanone was isolated.

Another method used for separating the tricosene removed the tricosanol and tricosanone from the tricosane by passing a solution of the crude mixture in a hydrocarbon solution through a column of dry silica gel sorbent. The dry silica gel sorbent selectively adsorbed the tricosanol and tricosanone, and left the tricosene in the eluent from the column with essentially no tricosanol and only traces of tricosanone.

Although this example speaks of our experiments with tricosene, the separation methods described in this example can also be used to isolate other olefins prepared in similar manners from other fatty acid derived ketones.

Example 9: Alkylation of Farnesane with Tricosene Using an Ionic Liquid Catalyst Farnesane (trimethyldodecane, a C15 isoalkane) was prepared by hydrogenation of farnesene (mixture of isomers, acquired from Sigma Aldrich) over a fixed bed of 20.7 wt % nickel on alumina catalyst (Johnson Matthey HTC500) at 320° F. (160° C.) and about 1700 psig (11721 kPa) using an LHSV of about 0.6-0.8 hr$^{-1}$.

400 ml of the prepared farnesane was combined with 40 ml n-butylpyridinium heptachlorodialuminate ionic liquid catalyst in a mechanically-stirred 2 liter reaction flask under inert atmosphere (nitrogen) and cooled to 4° C. on an ice bath. A mixture of 50 ml (39.6 g) 11-tricosene (C23 olefin, prepared as described in other examples) and 0.5 ml t-butyl chloride was added to the reaction flask over a period of 50 minutes, while the reaction temperature was maintained at 3-5° C. After an additional 10 minutes the stirring was stopped, the ionic liquid phase was allowed to settle out, and the hydrocarbon phase was decanted off. The hydrocarbon phase was stirred with ice and enough sodium bicarbonate (NaHCO$_3$) to neutralize the residual ionic liquid catalyst. Subsequently, the excess farnesane was distilled out at up to 149° C. and 2 torr on a RotoVap at 8 torr and 91° C., to isolate a yellow viscous oil. The isolated yellow viscous oil had the following properties, as shown in Table 5.

TABLE 5

| | |
|---|---|
| Viscosity Index | 129 |
| Kinematic Viscosity at 100° C., mm$^2$/s | 11.16 |
| Kinematic Viscosity at 40° C., mm$^2$/s | 79.93 |

TABLE 5-continued

| | |
|---|---|
| Pour Point, ° C. | −25 |
| Bromine Index, mg Br/100 g estimated from NMR | 500 |

A proton NMR of the yellow viscous oil confirmed that it was saturated and contained no vinylic protons. This confirmed that the yellow viscous oil was an alkylate, and not an oligomer.

$^{13}$C NMR normalized integrals of this isoalkane alkylate base oil are shown in Table 2 of this disclosure. In Example 9, 50.9% of the total $^{13}$C NMR integrals fall within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+(29.6-29.8 ppm).

Example 10: Alkylation of Farnesane with 1-Dodecene Using an Ionic Liquid Catalyst 400 ml of farnesane, prepared from farnesene as described in Example 9, was combined with 40 ml n-butylpyridinium heptachlorodialuminate ionic liquid catalyst and 0.1 ml t-butyl chloride in a mechanically-stirred 2 liter reaction flask under inert atmosphere (nitrogen) and cooled to 3° C. on an ice bath.

A mixture of 50 ml (37.4 g) 1-dodecene (C12) and 0.5 ml t-butyl chloride was added to the reaction flask over a period of 34 minutes, while the reaction temperature was maintained at about 3° C. The agitation was continued for an additional 10 minutes, then stirring was stopped, the ionic liquid phase was allowed to settle out, and the hydrocarbon phase was decanted off. The hydrocarbon phase was stirred overnight with water and enough sodium bicarbonate (NaHCO$_3$) to neutralize the residual ionic liquid catalyst. Subsequently, the hydrocarbon phase was concentrated on a RotoVap at 2 torr and 144° C., which removed the excess farnesane and isolated 75.8 g of a yellow oil.

The yellow oil product that was isolated was an isoalkane alkylate base oil having the properties as shown in Table 6.

TABLE 6

| | |
|---|---|
| Viscosity Index | 122 |
| Kinematic Viscosity at 100° C., mm$^2$/s | 9.854 |
| Kinematic Viscosity at 40° C., mm$^2$/s | 70.35 |
| Cloud Point, ° C. | <−60 |
| Pour Point, ° C. | −52 |
| Bromine Index, mg Br/100 g est. from NMR | <100 |

A proton NMR of this yellow oil product confirmed that it was completely saturated and contained no vinylic protons. The proton NMR confirmed that this yellow oil product was an alkylate, and not an oligomer.

Example 11: Alkylation of C6-C12 Isoalkanes with Tricosene (C23) Using an Ionic Liquid Catalyst A sample of C6-C12 isoalkanes was isolated as the naphtha cut of a saturated propylene oligomer product made by hydrogenating light propylene oligomers made by metallocene catalyzed oligomerization of propylene. The sample of C6-C12 isoalkanes comprised methyl pentane, dimethyl heptane, and trimethyl nonane. Gas chromatographic analysis of the sample of C6-C12 isoalkanes revealed the following composition: 38 wt % 2-methylpentane, 52 wt % dimethylheptane, 8 wt % trimethylnonane, and 2 wt % heavier isoalkanes.

600 ml (384 g) of the sample of the above mentioned C6-C12 isoalkane mixture was combined with 40 ml n-butylpyridinium heptachlorodialuminate ionic liquid catalyst in a mechanically-stirred 2 liter reaction flask under inert atmosphere (nitrogen) and cooled to 2° C. on an ice bath. A mixture of 60 ml (47.6 g) tricosene and 0.6 ml t-butyl chloride was added to the reaction flask over a period of about 1 hour, while the reaction temperature was maintained at about 2° C. The stirring was stopped, the ionic liquid phase was allowed to settle out, and the hydrocarbon phase was decanted off. The hydrocarbon phase was treated with water and enough sodium bicarbonate (NaHCO3) to neutralize the residual ionic liquid catalyst. Subsequently, the excess C6-C12 isoalkanes were distilled out as the hydrocarbon phase, and were concentrated on a RotoVap at 9 torr and 92° C., to isolate a yellowish isoalkane alkylate base oil.

A SIMDIS analysis of the isolated yellowish isoalkane alkylate base oil revealed that the isolated oil still contained significant amounts of material with a boiling point less than 200° C. The isolated yellowish isoalkane alkylate base oil was then heated to 125° C. in a stream of nitrogen for about 1 hour to remove residual light hydrocarbons and produce a final product. The final product was an isoalkane alkylate base oil having the properties as shown in Table 7.

TABLE 7

| | |
|---|---|
| Viscosity Index | 182 |
| Kinematic Viscosity at 100° C., mm$^2$/s | 5.047 |
| Kinematic Viscosity at 40° C., mm$^2$/s | 20.94 |
| Pour Point, ° C. | −26 |
| VI/KV100 | 36.06 |
| Bromine Index, mg Br/100 g | 1800 |

$^{13}$C NMR normalized integrals of this isoalkane alkylate base oil are also shown in Table 2 of this disclosure. In Example 11, 52.5% of the total $^{13}$C NMR integrals fall within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+ (29.6-29.8 Ppm).

It is notable that in all of the examples described above, no hydroisomerization dewaxing was used to make the isoalkane alkylate base oils. All of these examples of the isoalkane alkylate base oils were also made without any subsequent hydrogenation after the alkylating, yet still had low bromine indexes.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible subgeneric combinations of the listed components and mixtures thereof.

The invention illustratively disclosed herein suitably may be practiced in the absence of any element which is not specifically disclosed herein.

It is claimed:

1. An isoalkane alkylate base oil that is essentially free of olefins and aromatics and consists predominantly of long carbon chain molecules having a straight chain of no less than 12 carbon atoms and having at least one branch towards the middle of the straight chain wherein:
    a) the isoalkane alkylate base oil contains less than 10 wt % n-alkanes, less than 0.1 wt % olefinic hydrocarbons, and less than 0.1 wt % aromatic hydrocarbons;
    b) the at least one branch is a branched alkyl group containing 4 or more carbon atoms; and
    c) the long carbon chain molecules have two terminal linear unbranched alkyl groups each containing at least 4 carbons.

2. The isoalkane alkylate base oil of claim 1, wherein more than 25% of the total integral of the $^{13}$C NMR spectrum falls within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+(29.6-29.8 ppm).

3. The isoalkane alkylate base oil of claim 2, wherein more than 50% of the total integral of the $^{13}$C NMR spectrum falls within the $^{13}$C NMR resonances in the ranges for linear long chain alkyl groups.

4. The isoalkane alkylate base oil of claim 2, wherein the isoalkane alkylate base oil has a viscosity index greater than 90 and the total integral of the $^{13}$C NMR spectrum falling with the $^{13}$C NMR resonances in the ranges for linear long chain alkyl groups is from 26% to 80%.

5. The isoalkane alkylate base oil of claim 1, wherein the isoalkane alkylate base oil has a viscosity index from 91 to 200.

6. The isoalkane alkylate base oil of claim 1, wherein the isoalkane alkylate base oil has a bromine index less than 2000 mg Br/100 g.

7. The isoalkane alkylate base oil of claim 1, wherein the isoalkane alkylate base oil has a pour point less than −15° C.

8. The isoalkane alkylate base oil of claim 1, wherein the isoalkane alkylate base oil has a kinematic viscosity at 100° C. from 2 to 30 mm$^2$/s, a pour point less than 0° C., and a bromine index less than 2000 mg Br/100 g.

9. The isoalkane alkylate base oil of claim 1, wherein the branched alkyl group containing 4 or more carbons atoms is an isobutyl group, an isohexyl group, a tertiary butyl group, or a poly-branched nonyl group.

10. The isoalkane alkylate base oil of claim 1, wherein the two-terminal linear unbranched alkyl groups containing at least 4 carbons are n-butyl-, n-pentyl-, or nCnH2n+1-, where n is greater than or equal to 4.

* * * * *